(12) United States Patent
Hu et al.

(10) Patent No.: US 8,734,531 B2
(45) Date of Patent: May 27, 2014

(54) USE OF TEA-POLYPHENOL AND/OR TEA-PIGMENT AS DYE AND PRODUCTS THEREOF

(75) Inventors: Liu Hu, Zhejiang (CN); Hongying Lan, Zhejiang (CN)

(73) Assignee: Natural Medicine Institute of Zhejiang Yangshengtang Co., Ltd., Zhejiang (CN)

( * ) Notice: Subject to any disclaimer, the term of this patent is extended or adjusted under 35 U.S.C. 154(b) by 0 days.

(21) Appl. No.: 13/885,645

(22) PCT Filed: Nov. 18, 2011

(86) PCT No.: PCT/CN2011/082454
§ 371 (c)(1),
(2), (4) Date: May 28, 2013

(87) PCT Pub. No.: WO2012/065576
PCT Pub. Date: May 24, 2012

(65) Prior Publication Data
US 2013/0255009 A1  Oct. 3, 2013

(30) Foreign Application Priority Data
Nov. 19, 2010 (CN) .......................... 2010 1 0551117

(51) Int. Cl.
*A61Q 5/10* (2006.01)
(52) U.S. Cl.
USPC ................. 8/405; 8/406; 8/424; 8/435; 8/646

(58) Field of Classification Search
USPC ............................. 8/405, 406, 424, 435, 646
See application file for complete search history.

(56) References Cited

U.S. PATENT DOCUMENTS

| 7,550,014 | B2 * | 6/2009 | Greaves et al. | .................... 8/405 |
| 2010/0150857 | A1 * | 6/2010 | Guerin et al. | ................ 424/70.1 |

FOREIGN PATENT DOCUMENTS

| CN | 101164528 | 4/2008 |
| CN | 101280525 | 10/2008 |
| CN | 101431976 | 5/2009 |
| CN | 101791269 | 8/2010 |

OTHER PUBLICATIONS

International Search Report for PCT/CN2011/082454.

* cited by examiner

*Primary Examiner* — Eisa Elhilo
(74) *Attorney, Agent, or Firm* — Pillsbury Winthrop Shaw Pittman, LLP

(57) ABSTRACT

The present invention relates to the use of tea-polyphenol and/or tea-pigment as a dye and its products, and specifically relates to use of a combination of tea-polyphenol and/or its oxidation product, tea-pigment, as a dye active and a metal salt for dyeing human or animal hair, or use of the combination for the preparation of a product for dyeing human or animal hair, and to a hair dyeing product or a hair dyeing combination product comprising tea-polyphenol and/or tea-pigment. The present invention has the advantages including good dyeing fastness, natural and bright, not-stimulating, not-allergenic, not-mutagenic, no damage to hair, simple to operate and short time consuming.

8 Claims, No Drawings

USE OF TEA-POLYPHENOL AND/OR TEA-PIGMENT AS DYE AND PRODUCTS THEREOF

CROSS-REFERENCE TO RELATED APPLICATIONS

This is the U.S. National Stage of PCT/CN2011/082454, filed Nov. 18, 2011, which in turn claims priority to Chinese Patent Application No. 201010551117.0, filed Nov. 19, 2010, the entire contents of all applications are incorporated herein by reference in their entireties.

TECHNICAL FIELD

The present invention belongs to the technical field of cosmetic industry, and specifically relates to use of tea-polyphenol and/or its oxidation product, tea-pigment, as dye for the preparation of a product for dyeing human or animal hair, and to hair dyeing products comprising tea-polyphenol and/or its oxidation product, tea-pigment, as dye.

BACKGROUND ART

As the living standard improves, hair dyeing has become one method for people to pursue vogue and beauty. According to the used materials, the hair dyeing agents sold presently on the market may be classified into three types: the first one is chemically synthesized hair dyeing agent that occupies most of the market share, wherein harmful substances such as thioglycolic acid, p-phenylenediamine and hydrogen peroxide are added; the second one is chemically synthesized hair dyeing agent with "natural" concept that occupies a little of the market share, wherein some plant ingredients are added, but p-phenylenediamine and the like are also included therein; and the third one is natural dyeing agent that occupies a thimbleful of the market share. The foregoing two types of hair dyeing agents can be used in a convenient and quick way, but they are more allergenic and potentially carcinogenic, and damage the hair. Although the natural hair blackening agents sold presently on the market are safe and not-stimulating, for example, "Sanjing" sorghum red natural hair dyeing agent, "Yipin" natural hair dyeing agent, "Laorentou" galla rhois gallnut natural hair dyeing agent, clove hair dyeing agent and the like as manufactured in China, which are respectively three-part or two-part products, due to the limitation of compatibility among the active ingredients used therein, it is difficult to form a uniform composition by mixing various agents together during the preparation, or it is difficult to achieve the desired effect by applying a mixture of various agents once during the actual hair dyeing operation, so all of them require two or three or even more times of application and washing, which leads to a quite complicated operation and a hair dyeing time of up to 2.5 hours, with poor acceptance of the consumers.

Tea-polyphenol is a mixture of fused ring aromatic hydrocarbons extracted from tea. These fused ring aromatic hydrocarbons, based on their chemical structures, can be divided into flavanols, hydroxy-[4]-flavanols, anthocyanins, flavonoids, flavonols, and phenolic acids and the like. Among them, flavanols (mainly catechins) are the most important, accounting for 60% to 80% of the total mass of the polyphenols; catechins mainly consist of the following several monomers: epigallocatechin (EGC), epicatechin (EC), epigallocatechin gallate (EGCG), epicatechin gallate (ECG) and the like, which structural formulae are given as follows:

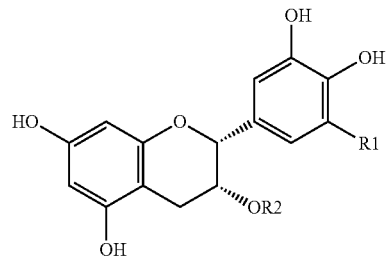

1. R1 = R2 = H  Epicatechin
2. R1 = OH, R2 = H Epigallocatechin
3. R1 = H, R2 = galloyl Epicatechin gallate
4. R1 = OH, R2 = galloyl Epigallocatechin gallate Tea-pigment is derived from the oxidation of catechins and their derivatives in tea, which molecular structure retains the main structural feature of catechins. Tea-pigment is also a complex including theaflavins, thearubigins and theabrownins. Tea-pigment can be isolated and purified from tea or prepared by using an in vitro simulated oxidation system. Tea-polyphenol and its oxidation product (tea-pigment) have many important biological and pharmacodynamic activity, mainly including anti-oxidation, cardiovascular protection, prevention and treatment of radiation injury, anti-allergy, suppression and resistance to virus and bacteria infraction, as well as diuretic, fatigue releasing, beautifying and skin care, tooth protection and improving eyesight, and refreshing and the like. Chinese Patent such as CN101164528B discloses the preparation of natural hair dyeing product using plant pigment catechu. However, catechu pigment has a complicated composition, moreover, according to the preparation and use methods disclosed therein, it is found that the natural hair dyeing product provided therein has a relatively poor effect of hair dyeing, in particular of blackening white hair, and is difficult to meet the demand of the users. Therefore, to develop the use of tea-polyphenol and/or tea-pigment as dye active for dyeing human or animal hair and its corresponding products can meet the current market demand.

Contents of the Invention

After study, the present inventors have surprisingly found that tea-polyphenol or its oxidation product, tea-pigment, can be used as a dye active for the preparation of a product for dyeing animal or human hair. The mechanism to generate the use of the present invention is that tea-polyphenol or its oxidation product, tea-pigment, can react with metal ion, to generate a colored complex, for example, it can react with iron ion to generate a black complex. Therefore, by using tea-polyphenol or its oxidation product, tea-pigment, naturally existed in tea as a dye active, and a metal salt as a mordant active, it is possible to dye human and animal hair from white to other colors such as black. Based on the above finding, the present inventors completed the present invention.

In the first aspect, the present invention relates to use of a combination of tea-polyphenol and/or its oxidation product, tea-pigment, as a dye active and a metal salt for dyeing human or animal hair, or use of the combination for the preparation of a product for dyeing human or animal hair.

In one embodiment of the aspect, the tea-polyphenol is selected from one or more of polyphenols in tea including flavanols, anthocyanins, flavonoids, flavonols and phenolic acids etc.

In another embodiment of the aspect, the tea-polyphenol is flavanols, and is selected from one or more of epigallocatechin, epicatechin, epigallocatechin gallate and epicatechin gallate.

In another embodiment of the aspect, the tea-pigment is selected from one or more of theaflavins, thearubigins and theabrownins.

In another embodiment of the aspect, the metal salt is a divalent metal salt.

In another embodiment of the aspect, the divalent metal salt is a ferrous salt.

In another embodiment of the aspect, the ferrous salt is selected from one or more of ferrous sulfate, ferrous chloride, ferrous nitrate, ferrous gluconate, ferrous lactate and ferrous fumarate.

In another embodiment of the aspect, the amount of the ferrous salt (based on ferrous ion), relative to the total weight of the hair dyeing product, is 1~10%, for example 2~8%.

In any of the above embodiments, the amount of the tea-polyphenol (for example, based on catechin), relative to the total weight of the hair dyeing product, is 0.5~15%, 1~10%, 2~8%, 3~5% or 4%.

In any of the above embodiments, the amount of the tea-pigment (for example, based on theaflavins), relative to the total weight of the hair dyeing product, is 0.5~15%, 1~10%, 2~8%, 3~5% or 4%.

In the second aspect, the present invention relates to a product for dyeing human or animal hair, which comprises an effective amount of tea-polyphenol and/or its oxidation product, tea-pigment, and an effective amount of a metal salt, as well as auxiliary components acceptable in hair dyeing product.

In one embodiment of the aspect, the tea-polyphenol is selected from one or more of polyphenols in tea including flavanols, anthocyanins, flavonoids, flavonols and phenolic acids etc.

In another embodiment of the aspect, the tea-polyphenol is flavanols, and is selected from one or more of epigallocatechin, epicatechin, epigallocatechin gallate and epicatechin gallate.

In another embodiment of the aspect, the tea-pigment is selected from one or more of theaflavins, thearubigins and theabrownins.

In another embodiment of the aspect, the metal salt is a divalent metal salt.

In another embodiment of the aspect, the divalent metal salt is a ferrous salt.

In another embodiment of the aspect, the ferrous salt is selected from one or more of ferrous sulfate, ferrous chloride, ferrous nitrate, ferrous gluconate, ferrous lactate and ferrous fumarate.

In another embodiment of the aspect, the amount of the ferrous salt (based on ferrous ion), relative to the total weight of the hair dyeing product, is 1~10%, for example 2~8%.

In any of the above embodiments, the amount of the tea-polyphenol (for example, based on catechin), relative to the total weight of the hair dyeing product, is 0.5~15%, 1~10%, 2~8%, 3~5% or 4%.

In any of the above embodiments, the amount of the tea-pigment (for example, based on theaflavins), relative to the total weight of the hair dyeing product, is 0.5~15%, 1~10%, 2~8%, 3~5% or 4%.

In any of the above embodiments, the auxiliary components acceptable in hair dyeing product comprise a hair softener.

In the third aspect, the present invention relates to a combination product for dyeing human or animal hair, which comprises a hair softening preparation, a dye preparation and a mordant preparation, wherein the dye preparation comprises an effective amount of tea-polyphenol and/or its oxidation product, tea-pigment, and the mordant preparation comprises an effective amount of a metal salt and an antioxidant. Optionally, the combination product further comprises instructions on how to use the hair softening preparation, the dye preparation and the mordant preparation.

In one embodiment of the aspect, the tea-polyphenol is selected from one or more of polyphenols in tea, including flavanols, anthocyanins, flavonoids, flavonols and phenolic acids etc.

In another embodiment of the aspect, the tea-polyphenol is flavanols, and is selected from one or more of epigallocatechin, epicatechin, epigallocatechin gallate and epicatechin gallate.

In another embodiment of the aspect, the tea-pigment is selected from one or more of theaflavins, thearubigins and theabrownins.

In another embodiment of the aspect, the metal salt is a divalent metal salt.

In another embodiment of the aspect, the divalent metal salt is a ferrous salt.

In another embodiment of the aspect, the ferrous salt is selected from one or more of ferrous sulfate, ferrous chloride, ferrous nitrate, ferrous gluconate, ferrous lactate and ferrous fumarate.

In another embodiment of the aspect, the amount of the ferrous salt (based on ferrous ion), relative to the total weight of the hair dyeing product, is 1~10%, for example 2~8%.

In any of the above embodiments, the amount of the tea-polyphenol (for example, based on catechin), relative to the total weight of the hair dyeing product, is 0.5~15%, 1~10%, 2~8%, 3~5% or 4%.

In any of the above embodiments, the amount of the tea-pigment (for example, based on theaflavins), relative to the total weight of the hair dyeing product, is 0.5~15%, 1~10%, 2~8%, 3~5% or 4%.

According to the combination product of the aspect, the antioxidant includes, but not limited to, ascorbic acid or salts thereof, cysteine or derivatives and salts thereof, for example, ascorbic acid, sodium ascorbate, cysteine, cysteine hydrochloride, N-acetylcysteine, reduced glutathione and the like. In one embodiment of the aspect, the antioxidant is selected from cysteine or derivatives and salts thereof. In one embodiment of the aspect, the antioxidant is selected from D-cysteine, L-cysteine, DL-cysteine, N-acetylcysteine, and salts thereof. In one embodiment of the aspect, the antioxidant is selected from cysteine hydrochloride. According to the combination product of the aspect, the antioxidant may be used alone or in a mixture of any of the above antioxidants. According to the combination product of the aspect, the amount of the antioxidant, relative to the total weight of the mordant preparation, is 0.1~2% by weight. In one embodiment of the aspect, the amount of the antioxidant, relative to the total weight of the mordant preparation, is 0.2~1% by weight.

According to the combination product of the aspect, the dye preparation and/or the mordant preparation further comprise a penetration enhancer and a thickener (i.e., a viscosity adjuster useful for adjusting the state of fluid (e.g., liquid, semi-solid)), and optionally a preservative.

According to the combination product of the aspect, the penetration enhancer in the mordant preparation includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer may be one or more selected from oleyl alcohol, dodecyl sulfate, dodecyl sulfonate or other anionic surfactant, fatty alcohol ether or other nonionic surfactant, cocamido propyl betaine or other amphoteric surfactant. In one embodiment, the penetration enhancer may be one or more selected from oleyl alcohol, dodecyl sulfate or other anionic surfactant, fatty alcohol ether or other nonionic surfactant, cocamido propyl betaine or other amphoteric surfactant. According to the combination product of the present invention, the penetration enhancer may be used alone or in a mixture of any of the above penetration enhancers. In one embodiment, the amount of the penetration enhancer, relative to the total weight of the mordant preparation, is 1~10% by weight. In one embodiment, the amount of the penetration enhancer, relative to the total weight of the mordant preparation, is 2~8% by weight.

According to the combination product of the aspect, the thickener in the mordant preparation includes, but not limited to, one or more selected from fatty alcohols or high molecular polymers including carbomer, hydroxyethyl cellulose, hydroxypropylmethyl cellulose and the like. The weight percent of the thickener in the mordant preparation can be determined by a person skilled in the art according to the teaching of the present invention in combination with the prior art. In one embodiment, the amount of the thickener, relative to the total weight of the mordant preparation, is 1~10% by weight. In one embodiment, the amount of the thickener, relative to the total weight of the mordant preparation, is 2~8% by weight.

According to the combination product of the aspect, it further comprises a preservative. The preservative in the mordant preparation includes, but not limited to, paraben esters, for example, methylparaben, ethylparaben, propylparaben and butylparaben. The preservative may be used alone or in a mixture of any of the above preservatives, for example, a mixture of methylparaben and propylparaben in any proportion. The weight percent of the preservative in the mordant preparation can be determined by a person skilled in the art according to the teaching of the present invention in combination with the prior art. In one embodiment, the amount of the preservative, relative to the total weight of the mordant preparation, is 0.1~0.8% by weight. In one embodiment, the amount of the preservative, relative to the total weight of the mordant preparation, is 0.2~0.6% by weight.

According to the combination product of the aspect, the mordant preparation is in the form of emulsion, paste or gel.

According to the combination product of the aspect, the penetration enhancer in the dye preparation includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer may be one or more selected from oleyl alcohol, dodecyl sulfate, dodecyl sulfonate or other anionic surfactant, fatty alcohol ether or other nonionic surfactant, cocamido propyl betaine or other amphoteric surfactant. In one embodiment, the penetration enhancer may be one or more selected from oleyl alcohol, dodecyl sulfate or other anionic surfactant, fatty alcohol ether or other nonionic surfactant, cocamido propyl betaine or other amphoteric surfactant. According to the combination product of the present invention, the penetration enhancer may be used alone or in a mixture of any of the above penetration enhancers. In one embodiment, the amount of the penetration enhancer, relative to the total weight of the dye preparation, is 2~15% by weight. In one embodiment, the amount of the penetration enhancer, relative to the total weight of the dye preparation, is 3~10% by weight.

According to the combination product of the aspect, the thickener in the dye preparation includes, but not limited to, one or more selected from fatty alcohols or high molecular polymers including carbomer, hydroxyethyl cellulose, hydroxypropylmethyl cellulose and the like. In one embodiment, the weight percent of the thickener in the dye preparation can be determined by a person skilled in the art according to the teaching of the present invention in combination with the prior art. In one embodiment, the amount of the thickener, relative to the total weight of the dye preparation, is 1~10% by weight. In one embodiment, the amount of the thickener, relative to the total weight of the dye preparation, is 2~8% by weight.

According to the combination product of the present invention, the preservative in the dye preparation includes, but not limited to, nipagin esters, for example, methylparaben, ethylparaben, propylparaben and butylparaben. The preservative may be used alone or in a mixture of any of the above preservatives, for example, a mixture of methylparaben and propylparaben in any proportion. The weight percent of the preservative in the dye preparation can be determined by a person skilled in the art according to the teaching of the present invention in combination with the prior art. In one embodiment, the amount of the preservative, relative to the total weight of the dye preparation, is 0.1~0.8% by weight. In one embodiment, the amount of the preservative, relative to the total weight of the dye preparation, is 0.2~0.6% by weight.

According to the combination product of the aspect, the dye preparation is in the form of emulsion, paste or gel.

In one specific embodiment of the aspect, the dye preparation comprises an effective amount of tea-polyphenol and/or tea-pigment, cetyl/stearyl alcohol, Ceteareth-6, sodium dodecyl sulfate, lanolin, white vaseline, sodium sulfite, EDTA-2Na, methylparaben and propylparaben; and the mordant formulations comprises an effective amount of ferrous sulfate, cetyl/stearyl alcohol, Ceteareth-6, methylparaben, propylparaben and cysteine hydrochloride.

In the fourth aspect, the present invention relates to a combination product for dyeing human or animal hair, which comprises a hair softening preparation and a dye preparation, wherein the dye preparation comprises an effective amount of tea-polyphenol and/or its oxidation product, tea-pigment, and an effective amount of a metal salt and an antioxidant. Optionally, the combination product further comprises instructions on how to use the hair softening preparation and the dye preparation.

In one embodiment of the aspect, the tea-polyphenol is selected from one or more of polyphenols in tea including flavanols, anthocyanins, flavonoids, flavonols and phenolic acids.

In another embodiment of the aspect, the tea-polyphenol is flavanols, and is selected from one or more ofepigallocatechin, epicatechin, epigallocatechin gallate and epicatechin gallate.

In another embodiment of the aspect, the tea-pigment is selected from one or more of theaflavins, thearubigins and theabrownins.

In another embodiment of the aspect, the metal salt is a divalent metal salt.

In another embodiment of the aspect, the divalent metal salt is a ferrous salt.

In another embodiment of the aspect, the ferrous salt is selected from one or more of ferrous sulfate, ferrous chloride, ferrous nitrate, ferrous gluconate, ferrous lactate and ferrous fumarate.

In another embodiment of the aspect, the amount of the ferrous salt (based on ferrous ion), relative to the total weight of the hair dyeing product, is 1~10% by weight, for example 2~8%.

In any of the above embodiments of the aspect, the amount of the tea-polyphenol (for example, based on catechin), relative to the total weight of the hair dyeing product, is 0.5~15%, 1~10%, 2~8%, 3~5% or 4%.

In any of the above embodiments of the aspect, the amount of the tea-pigment (for example, based on theaflavins), relative to the total weight of the hair dyeing product, is 0.5~15%, 1~10%, 2~8%, 3~5% or 4% by weight.

According to the combination product of the aspect, the antioxidant includes, but not limited to, ascorbic acid or salts thereof, cysteine or derivatives and salts thereof, for example, sulfites, bisulfites, ascorbic acid, sodium ascorbate, cysteine and its salts or derivatives (for example, cysteine hydrochloride, N-acetylcysteine), reduced glutathione and the like. In one embodiment, the antioxidant is selected from cysteine or derivatives and salts thereof. In one embodiment, the antioxidant is selected from D-cysteine, L-cysteine, DL-cysteine, N-acetylcysteine, and salts thereof. In one embodiment, the antioxidant is selected from cysteine hydrochloride. According to the combination product of the present invention, the antioxidant may be used alone or in a mixture of any of the above antioxidants. In on embodiment, the weight percent of the antioxidant in the dye preparation can be determined by a person skilled in the art according to the teaching of the present invention in combination with the prior art. According to the combination product of the present invention, the amount of the antioxidant, relative to the total weight of the dye preparation, is 0.1~8% by weight, for example, 0.2~5% by weight, for example, 0.5~2.5% by weight.

According to the combination product of the aspect, the dye preparation further includes a penetration enhancer and a thickener, and optionally a preservative.

According to the combination product of the aspect, the penetration enhancer in the dye preparation includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer may be one or more selected from oleyl alcohol, dodecyl sulfate, dodecyl sulfonate or other anionic surfactant, fatty alcohol ether or other nonionic surfactant, cocamido propyl betaine or other amphoteric surfactant. In one embodiment, the penetration enhancer may be one or more selected from oleyl alcohol, dodecyl sulfate or other anionic surfactant, fatty alcohol ether or other nonionic surfactant, cocamido propyl betaine or other amphoteric surfactant. According to the combination product of the present invention, the penetration enhancer may be used alone or in a mixture of any of the above penetration enhancers. In one embodiment, the amount of the penetration enhancer, relative to the total weight of the dye preparation, is 1~30% by weight. In one embodiment, the amount of the penetration enhancer, relative to the total weight of the dye preparation, is 2~20% by weight.

According to the combination product of the aspect, the thickener (i.e., a viscosity adjuster useful for adjusting the state of fluid (e.g., liquid, semi-solid)) in the dye preparation includes, but not limited to, one or more selected from fatty alcohols or high molecular polymers including carbomer, hydroxyethyl cellulose, hydroxypropylmethyl cellulose and the like. The weight percent of the thickener in the dye preparation can be determined by a person skilled in the art according to the teaching of the present invention in combination with the prior art. In one embodiment, the amount of the thickener, relative to the total weight of the dye preparation, is 1~15% by weight. In one embodiment, the amount of the thickener, relative to the total weight of the dye preparation, is 2~10% by weight.

According to the combination product of the aspect, it may further comprise a preservative. The preservative includes, but not limited to, nipagin esters, for example, methylparaben, ethylparaben, propylparaben and butylparaben. The preservative may be used alone or in a mixture of any of the above preservatives, for example, a mixture of methylparaben and propylparaben in any proportion. The weight percent of the preservative in the dye preparation can be determined by a person skilled in the art according to the teaching of the present invention in combination with the prior art. In one embodiment, the amount of the preservative, relative to the total weight of the dye preparation, is 0.1~1.5% by weight. In one embodiment, the amount of the preservative, relative to the total weight of the dye preparation, is 0.2~0.8% by weight.

In one specific embodiment of the aspect, the dye preparation comprises an effective amount of tea-polyphenol, ferrous sulfate, cetyl/stearyl alcohol, Ceteareth-6, sodium dodecyl sulfate, cysteine hydrochloride, methylparaben and propylparaben.

In any aspect of the present invention, the hair softener may include, for example, one or more selected from a disulfide linkage reducing agent, an alkalizer, a penetration enhancer, and a thickener.

The disulfide linkage reducing agent includes, but not limited to, one or more selected from acetylcysteine or derivatives and salts thereof, urea, thiosulfates, sulfites, and bisulfites. In one embodiment, the disulfide linkage reducing agent is selected from acetylcysteine or salts thereof, cysteine or hydrochloride thereof, reduced glutathione, sulfites, and bisulfites. In one embodiment, the amount of the disulfide linkage reducing agent, relative to the total weight of the softener part, is 2~25% by weight. In one embodiment, the amount of the disulfide linkage reducing agent, relative to the total weight of the softener part, is 4~15% by weight.

The alkalizer is selected from one or more of the following alkalizers: ornithine, arginine, lysine, ammonia, ethanolamines (for example, monoethanolamine, diethanolamine, triethanolamine), alkyl alcohol amide, hydroxides or compositions containing carbonate. In one embodiment, the amount of the alkalizer in the softener part, relative to the total weight of the softener part, is 0.5~20% by weight. In one embodiment, the amount of the alkalizer in the softener part, relative to the total weight of the softener part, is 2~18% by weight.

The softener part further comprises a penetration enhancer. The penetration enhancer in the softener part includes, but not limited to, chemical penetration enhancers including azone and homologues thereof, organic acids and esters thereof, organic solvents, surfactants such as anionic surfactants, nonionic surfactants, and amphoteric surfactants; Chinese medicine penetration enhancers including terpenes, essential oils, lactone and the like; and any combination of the foregoing. In one embodiment, the penetration enhancer in the softener part may be one or more selected from oleyl alcohol, dodecyl sulfate, dodecyl sulfonate or other anionic surfactant, fatty alcohol ether or other nonionic surfactant, cocamido propyl betaine or other amphoteric surfactant. In one embodiment, the penetration enhancer in the softener part may be one or more selected from oleyl alcohol, dodecyl sulfate or other anionic surfactant, fatty alcohol ether or other nonionic surfactant, cocamido propyl betaine or other amphoteric surfactant. According to the present invention, the penetration enhancer in the softener part may be used alone or in a mixture of any of the above penetration enhancers. For example, the penetration enhancer may be one or more selected from sodium dodecyl sulfate, sodium lauryl ether sulfate and cocamido propyl betaine. In one embodiment, the amount of the penetration enhancer in the softener part, relative to the total weight of the softener part, is 1~10% by weight. In one embodiment, the amount of the penetration enhancer in the softener part, relative to the total weight of the softener part, is 2~8% by weight.

According to the present invention, the softener part further comprises a thickener (i.e., a viscosity adjuster useful for adjusting the state of fluid (e.g., liquid, semi-solid). The thickener in the softener part includes, but not limited to, one or more selected from fatty alcohols or high molecular polymers including carbomer, hydroxyethyl cellulose and the like. The weight percent of the thickener in the softener of the hair dyeing product, can be determined by a person skilled in the art according to the teaching of the present invention in combination with the prior art. In one embodiment, the amount of the thickener in the softener part, relative to the total weight of the softener part, is 0.1~2% by weight. In one embodiment, the amount of the thickener in the softener part, relative to the total weight of the softener part, is 0.2~1% by weight.

According to the present invention, the softener part is in the form of emulsion, paste or gel.

In one specific embodiment of the present invention, the hair softening preparation comprises a hair-softening effective amount of N-acetylcysteine, sodium sulfite, sodium dodecyl sulfate, carbomer, EDTA-2Na and monoethanolamine.

Unless otherwise definitely defined in the present specification, the technical terms used in the present invention have their well-recognized meanings in the art, or have their general meanings as understood by a person skilled in the art.

As used herein, the term "effective amount" refers to the amount of the component related by said term as required to achieve its function.

As used herein, the term "tea-polyphenol" refers to one or more polyphenols in tea, including flavanols (mainly catechins), anthocyanins, flavonoids, flavonols and phenolic acids etc., or only refers to one or more catechins selected from the monomers EGC, EC, EGCG and ECG.

As used herein, the term "tea-pigment" refers to an oxidation products of tea-polyphenol, which may be one or more selected from theaflavins, thearubigins and theabrownins.

As used herein, tea-polyphenol and catechin can be derived from natural plant tea leaves, which can be prepared by means of various known methods in the prior art. They have been on sale as goods, in which the amount of catechin is up to 5%~99% (for example, Ling Yichun et al, Chinese tea, 2010, 5:12-14; and Li Daxiang et al, Natural Product Research and Development, 2006, 18:171-181). These substances can be identified by known methods and techniques in this field.

As used herein, the oxidation product (i.e., tea-pigment) of tea-polyphenol can be derived from natural plant tea leaves, which can be isolated and purified from tea, or can be prepared by using an in vitro simulated oxidation system (for example, Zhang Jianyong, Chinese Tea, 2009, 9:8-10). Tea-pigment can also be prepared by means of various known methods in the prior art. It has been on sale as goods, with purity of above 90%. These substances can be identified by known methods and techniques in this field.

According to the present invention, when the tea-polyphenol and/or its oxidation product, tea-pigment, is used as dye for blackening hair, it can be used in combination with other natural extracts (for example, galla rhois gallnut extract, tannins and gallic acid).

When implementing the present invention, the product or combination product used for dyeing human or animal hair can be prepared into a three-part products.

The first part is called as a hair softener (or a softening preparation). Since tea-polyphenol and/or its oxidation product, tea-pigment, as dye molecule enters into the inside of hair at a relatively slow speed, when implementing the present invention, the hair can be firstly softened to enable the dye molecule easy to enter into the inside of the hair and thereby shorten the hair dyeing time peirod. As the hair softener, the softener used in commercially available natural hair dyeing agents, for example, the softening preparations in "Yipin" natural hair dyeing agent and "Laorentou" galla rhois gallnut natural hair dyeing agent, can be used.

The second part is called as a dye agent (or a dye preparation), which takes a colorizing effect. The dye agent can include tea-polyphenol and/or its oxidation product (tea-pigment) as its principal active components. By adding conventional substances that can be used in contact with skin (for example, which do not produce side effects such as skin stimulation), in particular those used in topical skin products, such as diluents, surfactants, thickeners and the like that can be used in cosmetics, the dye agent can be prepared into any formulation form suitable for hair dyeing, for example, the form of solution, emulsion, paste, cream or gel.

The third part is called as a mordant agent (or a metal ion agent or a mordant preparation), wherein the metal ion is chelated with a dye active to form a larger molecule, which changes the development color of the dye, and meanwhile makes the dye molecule even larger, so that the dye molecule is even difficult to bleed out from the hair after dyeing, and thereby achieves the purpose of permanent hair dyeing. The mordant agent includes a ferrous ion-containing compound as its principal active component. In the course of hair dyeing, ferrous ion is oxidized by air into ferric ion and complexed with tea-polyphenol and its oxidation product, tea-pigment, to form a black complex. By adding conventional substances that can be used in contact with skin (for example, which do not produce side effects such as skin stimulation), in particular those used in topical skin products, especially, such as diluents, surfactants, thickeners and the like that can be used in cosmetics, the mordant agent can be prepared into any formulation form suitable for hair dyeing, for example, the form of solution, emulsion, paste, cream or gel.

When the hair dyeing product is a three-part product, the weight percent of tea-polyphenol and/or tea-pigment relative to the total weight of the hair dyeing product refers to the weight percent of tea-polyphenol and/or tea-pigment relative to the weight of the dye preparation (i.e., the second part); the weight percent of ferrous salt (based on ferrous ion) relative to the total weight of the hair dyeing product refers to the weight percent of ferrous salt (based on ferrous ion) relative to the weight of the mordant preparation (i.e., the third part).

When implementing the present invention, the product or combination product used for dyeing human or animal hair can also be prepared into a two-part product.

The first part may be the same as the above first part, i.e., the softening preparation, in the three-part product.

The second part is a dye preparation, i.e., a uniform and stable composition formulated by mixing the above dye preparation and the above mordant preparation (i.e., the metal ion agent) in the three-part product, which includes tea-polyphenol and/or its oxidation product, tea-pigment, as its dye active, and a metal ion (for example ferrous ion) as its mordant active. By adding conventional substances that can be used in contact with skin (for example, which do not produce side effects such as skin stimulation), in particular those used in topical skin products, especially, such as diluents, surfactants, thickeners and the like that can be used in cosmetics, the dye preparation can be prepared into any formulation form suitable for hair dyeing, for example, the form of solution, emulsion, paste, cream or gel.

When the hair dyeing product is a two-part product, the weight percent of tea-polyphenol and/or tea-pigment relative to the total weight of the hair dyeing product refers to the weight percent of tea-polyphenol and/or tea-pigment relative to the weight of the dye preparation (i.e., the second part); the weight percent of ferrous salt (based on ferrous ion) relative to the total weight of the hair dyeing product refers to the weight percent of ferrous salt (based on ferrous ion) relative to the weight of the dye preparation (i.e., the second part).

The use of the present invention can be implemented, or the product and the combination product of the present invention can be used, by using conventional methods and tools in this field.

The product and the combination product of the present invention are not only excellent in product stability, but also capable of accomplishing softening and dyeing in one step. The hair softening preparation, the dye preparation and the mordant preparation can be separately packaged and stored. When used, they are combined, and applied to hair, so that white hair can be dyed into various colors such as black. Thus, to a very great extent, the operation steps can be simplified, and the operation time can be shortened.

When being made into any formulation form, tea-polyphenol and its oxidation product (tea-pigment) according to the present invention can be used as dye in hair dyeing products. Any product will fall into the protection scope of the present invention if it includes tea-polyphenol and/or tea-pigment as one of its components or it is made from tea-polyphenol and/or tea-pigment only, as long as it is indicated or suggested, in the logo on its package or instructions and any other propaganda material, that tea-polyphenol and/or tea-pigment (or catechin) is used as the dye active.

Any product, which is prepared by using tea-polyphenol and its oxidation product (tea-pigment) alone or in combination with other active component or auxiliary material, will fall into the protection scope of the present invention only if it is used for hair dyeing.

MODE OF CARRYING OUT THE INVENTION

The present invention is further illustrated by the following examples, comparative examples and test examples. However, it shall be understood that these examples, comparative examples and test examples are only used to specifically set forth the present invention, rather than being understood that they are used to limit the present invention in any form.

Although many materials and operation methods used for achieving the object of the present invention are well known in the art, the present invention still makes a description as detailed as possible herein. It is clear to a person skilled in the art that, hereinafter, if not especially indicated, the materials and operation methods used in the present invention are well known in the art.

EXAMPLE 1

1) Softening preparation (formulated in a total amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of the balance of deionized water was added till 100 g, followed by mixing with stirring to make a gel.

2) Dye preparation (formulated in a total amount of 100 g): 4 g tea-polyphenol (98% of total polyphenol, 80% of total catechins, in which 70% of EGCG, purchased from Zhejiang Painuo Biotechnology Co., Ltd.), 5 g cetyl/stearyl alcohol, 5 g Ceteareth-6, 4 g sodium dodecyl sulfate, 2 g lanolin, 2 g white vaseline, 0.2 g sodium sulfite, 0.2 g EDTA-2Na, 0.25 g methylparaben, and 0.15 g propylparaben were mixed sufficiently to obtain a uniform mixture; then the balance of deionized water was added, followed by mixing with stirring to make a paste.

3) Mordant preparation (formulated in a total amount of 100 g): 5 g ferrous sulfate, 5 g cetyl/stearyl alcohol, 5 g Ceteareth-6, 4 g sodium dodecyl sulfate, 0.25 g methylparaben, 0.15 g propylparaben, and 0.5 g cysteine hydrochloride were mixed sufficiently to obtain a uniform mixture; then the balance of deionized water was added, followed by mixing with stirring to make a paste.

4) Experiment of dyeing hair bundle: in use, the first part, the second part and the third part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable. The experimental results were given in the following test examples.

EXAMPLE 2

1) Softening preparation (formulated in a total amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of the balance of deionized water was added till 100 g, followed by mixing with stirring to make a gel.

2) Dye preparation (formulated in a total amount of 100 g): 2 g tea-polyphenol (98% of total polyphenol, 80% of total catechins, in which 60% of EGCG, purchased from Zhejiang Painuo Biotechnology Co., Ltd.), 2 g tea-pigment (purchased from Zhejiang Painuo Biotechnology Co., Ltd.), 5 g cetyl/stearyl alcohol, 5 g Ceteareth-6, 4 g sodium dodecyl sulfate, 2 g lanolin, 2 g white vaseline, 0.2 g sodium sulfite, 0.2 g EDTA-2Na, 0.25 g methylparaben, and 0.15 g propylparaben were mixed sufficiently to obtain a uniform mixture; then the balance of deionized water was added, followed by mixing with stirring to make a paste.

3) Mordant preparation (formulated in a total amount of 100 g): 5 g ferrous sulfate, 5 g cetyl/stearyl alcohol, 5 g Ceteareth-6, 4 g sodium dodecyl sulfate, 0.25 g methylparaben, 0.15 g propylparaben, and 0.5 g cysteine hydrochloride were mixed sufficiently to obtain a uniform mixture; then the balance of deionized water was added, followed by mixing with stirring to make a paste.

4) Experiment of dyeing hair bundle: in use, the first part, the second part and the third part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable. The experimental results were given in the following test examples.

EXAMPLE 3

1) Softening preparation (formulated in a total amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of the balance of deionized water was added till 100 g, followed by mixing with stirring to make a gel.

2) Dye preparation (formulated in a total amount of 100 g): 4 g tea-pigment (purchased from Zhejiang Painuo Biotechnology Co., Ltd.), 5 g cetyl/stearyl alcohol, 5 g Ceteareth-6, 4 g sodium dodecyl sulfate, 2 g lanolin, 2 g white vaseline, 0.2 g sodium sulfite, 0.2 g EDTA-2Na, 0.25 g methylparaben, and 0.15 g propylparaben were mixed sufficiently to obtain a uniform mixture; then the balance of deionized water was added, followed by mixing with stirring to make a paste.

3) Mordant preparation (formulated in a total amount of 100 g): 5 g ferrous sulfate, 5 g cetyl/stearyl alcohol, 5 g Ceteareth-6, 4 g sodium dodecyl sulfate, 0.25 g methylparaben, 0.15 g propylparaben, and 0.5 g cysteine hydrochloride were mixed sufficiently to obtain a uniform mixture; then the balance of deionized water was added, followed by mixing with stirring to make a paste.

4) Experiment of dyeing hair bundle: in use, the first part, the second part and the third part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable.

EXAMPLE 4

1) Softening preparation (formulated in a total amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of deionized water was added till 100 g, followed by mixing with stirring to make a gel.

2) Dye preparation (formulated in a total amount of 100 g): 4 g tea-polyphenol (98% of total polyphenol, 70% of total catechins, in which 50% of EGCG, purchased from Zhejiang Painuo Biotechnology Co., Ltd.), 2 g gallic acid, 5 g cetyl/stearyl alcohol, 5 g Ceteareth-6, 4 g sodium dodecyl sulfate, 2 g lanolin, 2 g white vaseline, 0.2 g sodium sulfite, 0.2 g EDTA-2Na, 0.25 g methylparaben, and 0.15 g propylparaben were mixed sufficiently to obtain a uniform mixture; then the balance of deionized water was added, followed by mixing with stirring to make a paste.

3) Mordant preparation (formulated in a total amount of 100 g): 5 g ferrous sulfate, 5 g cetyl/stearyl alcohol, 5 g Ceteareth-6, 4 g sodium dodecyl sulfate, 0.25 g methylparaben, 0.15 g propylparaben, and 0.5 g cysteine hydrochloride were mixed sufficiently to obtain a uniform mixture; then the balance of deionized water was added, followed by mixing with stirring to make a paste.

4) Experiment of dyeing hair bundle: in use, the first part, the second part and the third part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable.

EXAMPLE 5

1) Softening Preparation (Formulated in a Total Amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of deionized water was added till 100 g, followed by mixing with stirring to make a gel.

2) Dye preparation (formulated in a total amount of 100 g): 4 g tea-polyphenol (98% of total polyphenol, 80% of total catechins, in which 70% of EGCG, purchased from Zhejiang Painuo Biotechnology Co., Ltd.), 4 g ferrous sulfate, 5 g cetyl/stearyl alcohol, 5 g Ceteareth-6, 4 g sodium dodecyl sulfate, 0.5 g cysteine hydrochloride, 0.25 g methylparaben, and 0.15 g propylparaben were mixed sufficiently to obtain a uniform mixture; then the balance of deionized water was added, followed by mixing with stirring to make a paste.

3) Experiment of dyeing hair bundle: in use, the first part and the second part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable.

EXAMPLE 6

1) Softening preparation (formulated in a total amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of deionized water was added till 100 g, followed by mixing with stirring to make a gel.

2) Dye preparation (formulated in a total amount of 100 g): 2 g epicatechin (EC, purity 99%, purchased from Zhejiang Painuo Biotechnology Co., Ltd.), 5 g cetyl/stearyl alcohol, 5 g Ceteareth-6, 4 g sodium dodecyl sulfate, 2 g lanolin, 2 g white vaseline, 0.2 g sodium sulfite, 0.2 g EDTA-2Na, 0.25 g methylparaben, and 0.15 g propylparaben were mixed sufficiently to obtain a uniform mixture; then the balance of deionized water was added, followed by mixing with stirring to make a paste.

3) Mordant preparation (formulated in a total amount of 100 g): 5 g ferrous sulfate, 5 g cetyl/stearyl alcohol, 5 g Ceteareth-6, 4 g sodium dodecyl sulfate, 0.25 g methylparaben, 0.15 g propylparaben, and 0.5 g cysteine hydrochloride were mixed sufficiently to obtain a uniform mixture; then the balance of deionized water was added, followed by mixing with stirring to make a paste.

4) Experiment of dyeing hair bundle: in use, the first part, the second part and the third part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable.

EXAMPLE 7

1) Softening preparation (formulated in a total amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of deionized water was added till 100 g, followed by mixing with stirring to make a gel.

2) Dye preparation (formulated in a total amount of 100 g): 2 g epigallocatechin (EGC, purity 99%, purchased from Zhejiang Painuo Biotechnology Co., Ltd.), 5 g cetyl/stearyl alcohol, 5 g Ceteareth-6, 4 g sodium dodecyl sulfate, 2 g lanolin, 2 g white vaseline, 0.2 g sodium sulfite, 0.2 g EDTA-2Na, 0.25 g methylparaben, and 0.15 g propylparaben were mixed sufficiently to obtain a uniform mixture; then the balance of deionized water was added, followed by mixing with stirring to make a paste.

3) Mordant preparation (formulated in a total amount of 100 g): 5 g ferrous sulfate, 5 g cetyl/stearyl alcohol, 5 g Ceteareth-6, 4 g sodium dodecyl sulfate, 0.25 g methylparaben, 0.15 g propylparaben, and 0.5 g cysteine hydrochloride were mixed sufficiently to obtain a uniform mixture; then the balance of deionized water was added, followed by mixing with stirring to make a paste.

4) Experiment of dyeing hair bundle: in use, the first part, the second part and the third part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable.

EXAMPLE 8

1) Softening preparation (formulated in a total amount of 100 g): 6 g N-acetylcysteine, 1 g sodium sulfite, 4 g sodium dodecyl sulfate, 0.5 g carbomer, and 0.2 g EDTA-2Na were mixed sufficiently to obtain a uniform mixture; then, a suitable amount of monoethanolamine was added to adjust the product to pH=9.5 (test paper), and the balance of deionized water was added till 100 g, followed by mixing with stirring to make a gel.

2) Dye preparation (formulated in a total amount of 100 g): 2 g anthocyanin (purity 98%, provided by a manufacturer (Ifrarel) in France), 5 g cetyl/stearyl alcohol, 5 g Ceteareth-6, 4 g sodium dodecyl sulfate, 2 g lanolin, 2 g white vaseline, 0.2 g sodium sulfite, 0.2 g EDTA-2Na, 0.25 g methylparaben, and 0.15 g propylparaben were mixed sufficiently to obtain a uniform mixture; then the balance of deionized water was added, followed by mixing with stirring to make a paste.

3) Mordant preparation (formulated in a total amount of 100 g): 5 g ferrous sulfate, 5 g cetyl/stearyl alcohol, 5 g Ceteareth-6, 4 g sodium dodecyl sulfate, 0.25 g methylparaben, 0.15 g propylparaben, and 0.5 g cysteine hydrochloride were mixed sufficiently to obtain a uniform mixture; then the balance of deionized water was added, followed by mixing with stirring to make a paste.

4) Experiment of dyeing hair bundle: in use, the first part, the second part and the third part were added in an equal volume to a non-metal vessel, and mixed with a non-metal bar to obtain a uniform mixture. Without the necessity of washing hair, the mixture was applied onto the hair with a comb repeatedly till uniform, and then kept for 20~30 minutes. The hair was washed with warm water, and then air dried or blow dried.

The results showed that the hair bundle dyed with the hair dyeing agent of the present example was good in chroma and fastness, and the sample was stable.

COMPARATIVE EXAMPLE 1

Sanjing Plant Hair Dyeing Agent

1) The Sanjing plant hair dyeing agent was a product purchased from the market, which was a three-part type product including 1# hair dyeing composition, 2# hair dyeing composition and 3# hair dyeing composition. 1# hair dyeing composition is liquid, 2# hair dyeing composition and 3# hair dyeing composition are powders.

2) Experiment of dyeing hair bundle: 1# hair dyeing composition was poured into a clean non-metal vessel, to which sorghum essence was then poured, followed by mixing uniformly. The resulting solution was applied onto the hair with a brush thoroughly and repeatedly till uniform, and then a cap was put on the hair, followed by keeping for 25~30 minutes (it was suggested that the temperature should be not lower than 20° C.). Thereafter, the hair was washed with warm water and wiped to dry. 2# hair dyeing composition (powder) was poured into a clean non-metal vessel, to which 50 ml clean water was added, followed by thoroughly mixing till uniform, and was applied onto the hair in a similar way to the application of 1# hair dyeing composition, and then kept for 10 minutes. Thereafter, the hair was washed with warm water and dried. 3# hair dyeing composition (powder) was used in a similar way to the operation of 2# hair dyeing composition, and then kept for 10 minutes. Thereafter, the hair was washed with warm water and wiped to dry.

COMPARATIVE EXAMPLE 2

Yinpin Natural Hair Dyeing Agent

1) The Yinpin natural hair dyeing agent was a product purchased from the market, which was a three-part type product including 1# hair dyeing composition, 2# hair dyeing composition and 3# hair dyeing composition, all of them is liquid.

2) Experiment of dyeing hair bundle: hair was washed with shampoo and wiped to dry. 1# hair dyeing composition was applied onto the hair repeatedly till uniform, then a shower cap was put on the hair, and the shower cap was covered with a dry towel, followed by uniformly heating with a hair dryer at a temperature that is slightly higher than body temperature (not lower than 40° C.) for 20~30 minutes. Thereafter, the hair was washed with warm water and wiped to dry. 2# hair dyeing composition was applied onto the hair in a similar way to the application of 1# hair dyeing composition. Without the use of a shower cap and heating, after waiting for 15~20 minutes, the hair was washed with warm water and wiped to dry. 3# hair dyeing composition was used in a similar way to the application of 2# hair dyeing composition. After waiting for 10 minutes, the hair was washed with warm water and wiped to dry.

COMPARATIVE EXAMPLE 3

Clove Hair Dyeing Agent

1) The clove hair dyeing agent was a product purchased from the market, which was a two-part type product including 1# hair dyeing composition and 2# hair dyeing composition, both of them are liquid.

2) Experiment of dyeing hair bundle: hair was washed with shampoo and wiped to dry. 1# hair dyeing composition was applied onto the hair repeatedly till uniform, and then a shower cap was put on the hair, followed by heating with a steam generator for 25~30 minutes. Thereafter, the hair was washed with warm water and wiped to dry. 2# hair dyeing composition was applied onto the hair in a similar way to the application of 1# hair dyeing composition. Without the use of a shower cap, the hair was directly heated with a steam generator for 20 minutes. Thereafter, the hair was washed with warm water and wiped to dry.

COMPARATIVE EXAMPLE 4

Hair Dyeing Product Formulated According to the Method Disclosed in CN 101164528B)

Preparation of catechu pigment: it was prepared in accordance with the example in CN 100591727C entitled "Method for refining powdered catechu dye by film separation technique and dyeing method thereof".

Step 1: at room temperature, adding commercially available catechu paste to 40 times of water, and heating to slight boiling for 30 min, thereby completely dissolving catechu paste in the boiling water, to obtain a solution of catechu paste.

Step 2: primarily filtering the solution of catechu paste using a steel wire screen of 180 meshes.

Step 3: placing a fast qualitative filter paper on a Buchner funnel, and filtering the solution through it using a vacuum pump.

Step 4: passing the solution (whose temperature was controlled to be below 35° C.) obtained in step 3 using a circulating pump through an outside-in polyvinylidene fluoride microfiltration membrane with a pore size of 0.2~0.5 μm (due to pressure, small molecular pigment which is effective for dyeing entered the inside of the membrane from its outside, whereas macromolecular impurities could not enter the inside of the membrane), while adjusting the operation pressure to be 0.04 MPa, returning the non-permeate back to the vessel containing the stock solution, and repeating the operation until almost no outflow occurred, thereby collecting a clear permeate.

Step 5: subjecting the clear permeate which had passed through the microfiltration membrane to vacuum concentration, to obtain a catechu dye solution having a solids content of 5~10%.

Step 6: evaporating the water in the concentrated catechu dye solution using a spray dryer, to obtain a refined catechu pigment powder having a high content of effective pigment ingredient.

Agent A: catechu pigment 20 g, ethanol 100 g, water added till 200 g;

Agent B: $FeSO_4.7H_2O$ 10 g, reduced iron powder 2.0 g, polyethylene glycol 10 g, carboxymethyl cellulose 2 g, acetic acid 0.3 g, lavender essence 0.2 g, water added to 200 g.

Hair dyeing method: agent A was applied uniformly onto washed hair, and kept at 40° C. for 30 min, then agent B was uniformly applied onto the hair, and kept for 20 min. Thereafter, the hair was washed and blow dried.

COMPARATIVE EXAMPLE 5

Hair Dyeing Product Formulated According to the Method Disclosed in CN 101164528B Preparation of catechu pigment: the same as that in Comparative Example 4.

Agent A: catechu pigment 10 g, ethanol 20 g, water added till 200 g;

Agent B: $FeSO_4.7H_2O$ 4 g, reduced iron powder 0.8 g, polyethylene glycol 6 g, carboxymethyl cellulose 4 g, acetic acid 1 g, lavender essence 0.2 g, water added till 200 g.

Hair dyeing method: agent A was applied uniformly onto washed hair, and kept at 40° C. for 20 min, then agent B was uniformly applied onto the hair, and kept for 10 min. Thereafter, the hair was washed and blow dried.

TEST EXAMPLE

Experiment on Chroma and Fastness of Hair Bundle and Experiment on Stability of Formulations 1. Test Method Hair bundle: white hairs taken from the top of head of the same person with white hairs.

Chroma of hair bundle: the dyed hairs were detected by using a chroma meter, and simultaneously observed by naked eyes.

Fastness of hair bundle: the dyed hairs were radiated in sunlight to investigate their sunlight-resistant fastness; the dyed hairs were washed with market-sold shampoo to investigate their washing-resistant fastness.

Stability of formulation: after being stored in an oven of 40° C. for two months, the formulation samples, which were respectively obtained in Example 1, Example 2, Comparative Example 1, Comparative Example 2, Comparative Example 3, Comparative Example 4 and Comparative Example 5, were taken out and then stored in a refrigerator of 0° C., after two months, the formulation samples were observed with regard to their state and used to hair dyeing experiment.

Repetitive use: after unsealed, the formulation samples were placed for 1 month, 2 months, 4 months and 6 months respectively, and then observed with regard to their state and subjected to hair dyeing experiment.

2. Experimental Results

The hairs were dyed according to the methods as described in Example 1, Example 2, Comparative Example 1, Comparative Example 2, Comparative Example 3, Comparative Example 4 and Comparative Example 5 respectively, and the stability and repetitive use of the five formulations were investigated.

The results of dyeing the hair bundle by using the hair dyeing agent of Example 1 were as follows: the dyed hair bundle was black as detected by using a chroma meter, and the case is the same as observed by naked eyes. The experimental results of fastness showed that: after being radiated in sunlight for 50 days and washed for 50 times, no discoloration was observed. The softening preparation, the dye preparation and the mordant preparation were subjected to stability experiments, and it was observed that the appearance thereof had no obvious change, and the dyeing results were consistent before and after investigation in the stability experiments. The experimental results of repetitive uses showed that: after placed for 1 month, 2 months, 4 months and 6 months when the formulations are unsealed, the softening preparation had no obvious change in appearance, and the dye preparation and the mordant preparation had no obvious change except that the portion at the open end in contact with air became discolored, while the dyeing results were consistent before and after the experiments.

The results of dyeing the hair bundle by using the hair dyeing agent of Example 2 were as follows: the dyed hair bundle was black as detected by using a chroma meter, and the case is the same as observed by naked eyes. The experimental results of fastness showed that: after being radiated in sunlight for 50 days and washed for 50 times, no discoloration was observed. The softening preparation, the dye preparation and the mordant preparation were subjected to stability experiments, and it was observed that the appearance thereof had no obvious change, and the dyeing results were consistent before and after investigation in the stability experiments. The experimental results of repetitive uses showed that: after placed for 1 month, 2 months, 4 months and 6 months when the formulations are unsealed, the softening preparation had no obvious change in appearance, and the dye preparation and the mordant preparation had no obvious change except that the portion at the open end in contact with air became discolored, while the dyeing results were consistent before and after the experiments.

The results of dyeing the hair bundle by using the hair dyeing agent of Comparative Example 1 were as follows: the hair bundle was dyed at 20° C. according to the instructions, and the colorizing effect was not ideal. The colorizing effect at 25° C. was relatively satisfactory. The dyed hair bundle was black as detected by using a chroma meter, and the case is the same as observed by naked eyes. The experimental results of fastness showed that: after being radiated in sunlight for 50 days and washed for 50 times, no discoloration was observed. 1# hair dyeing composition, 2# hair dyeing composition and 3# hair dyeing composition were all subjected to stability experiments, and it was observed that 1# hair dyeing composition significantly became dilute in appearance after investigation in the stability experiments, and 2# hair dyeing composition and 3# hair dyeing composition had no obvious change in appearance, and the hair bundle as dyed therewith at 25° C. was purple. The experimental results of repetitive uses showed that: on the second day after unsealing, 1# hair dyeing composition became turbid and discolored, 2# hair dyeing composition (powder) and 3# hair dyeing composition became discolored, and the hair bundle as dyed therewith at 25° C. was pale purple.

The results of dyeing the hair bundle by using the hair dyeing agent of Comparative Example 2 were as follows: the dyed hair bundle was black as detected by using a chroma meter, and the case is the same as observed by naked eyes. The experimental results of fastness showed that: after being radiated in sunlight for 50 days and washed for 50 times, no discoloration was observed. 1# hair dyeing composition, 2# hair dyeing composition and 3# hair dyeing composition were all subjected to stability experiments, and it was observed that the three compositions all significantly became dilute in appearance after investigation in the stability experiments, and the hair bundle as dyed therewith was purple. The experimental results of repetitive uses showed that: on the second day after unsealing, 1# hair dyeing composition, 2# hair dyeing composition and 3# hair dyeing composition became turbid and discolored, and the hair bundle as dyed therewith was pale purple.

The results of dyeing the hair bundle by using the hair dyeing agent of Comparative Example 3 were as follows: the dyed hair bundle was black as detected by using a chroma meter, and the case is the same as observed by naked eyes. The experimental results of fastness showed that: after being radiated in sunlight for 50 days and washed for 50 times, no discoloration was observed. 1# hair dyeing composition and 2# hair dyeing composition were both subjected to stability experiments, and it was observed that the two compositions both significantly became dilute in appearance after investigation in the stability experiments, and the hair bundle as dyed therewith was purple. The experimental results of repetitive uses showed that: on the second day after opening, 1# hair dyeing composition and 2# hair dyeing composition became turbid and discolored, and the hair bundle as dyed therewith was pale purple.

The results of dyeing the hair bundle by using the hair dyeing agent of Comparative Example 4 were as follows: the dyed hair bundle was not black as detected by using a chroma meter, and was light brownish red as observed by naked eyes. The experimental results of fastness showed that: discoloration was observed after being radiated in sunlight for 5 days, and the case is the same after being washed for 5 times. Agent A and agent B were both subjected to stability experiments, and it was observed that the appearance of agent A had no obvious change before and after investigation in the stability experiments, and, due to the limitation of ion resistance of the thickener used, agent B became stratified, and gradually became an aqua with the lapse of time, and the hair bundle as dyed therewith was lighter brown.

The results of dyeing the hair bundle by using the hair dyeing agent of Comparative Example 5 were as follows: the dyed hair bundle was not black as detected by using a chroma meter, and was extremely light brownish red as observed by naked eyes. The experimental results of fastness showed that: discoloration was observed after being radiated in sunlight for 5 days, and the case is the same after being washed for 5 times. Agent A and agent B were both subjected to stability experiments, and it was observed that the appearance of agent A had no obvious change before and after investigation in the stability experiments, and, due to the limitation of ion resistance of the thickener used, agent B became stratified, and gradually became an aqua with the lapse of time, and the hair bundle as dyed therewith was lighter brown.

The above results demonstrated that, as compared with Comparative Examples 1, 2, 3, 4 and 5, the hair bundle as dyed with the formulations of Example 1 and Example 2 was natural black, without discoloration for about 50 days, and the formulations were excellent in stability, and could be repetitively used for many times.

The difference in operating mode of the five formulations was listed in the following table.

| Test example | Whether the product needs to be formulated just before use | Times of washing hair | Times of applying formulation | Dyeing time*/min | Treatment time**/min |
|---|---|---|---|---|---|
| Example 1 | No | One | One | 30 | 45 |
| Example 2 | No | One | One | 30 | 45 |
| Com. Ex. 1 | Yes | Three | Three | 50 | 120 |
| Com. Ex. 2 | No | Four | Three | 60 | 110 |
| Com. Ex. 3 | No | Three | Two | 50 | 85 |
| Com. Ex. 4 | No | One | Two | 60 | 85 |
| Com. Ex. 5 | No | One | Two | 30 | 55 |

Notes:
*indicated the time required for retaining the hair dyeing agent on the hair;
**indicated the time required for formulating the product just before use, washing hair, applying the hair dyeing agent and retaining the hair dyeing agent on the hair.

From the above table, it could be seen that, according to the operating mode of Example 1 and Example 2, the hair softening and dyeing operations were carried out in one step. The hair softening preparation, the dye preparation and the mordant preparation could be separately packaged and stored. When used, they were combined, and applied to the hair, so that the times of washing and the times of applying could be decreased greatly. Thus, to a very great extent, the operation steps could be simplified, and the operation time could be shortened.

The invention claimed is:

1. A product for dyeing human or animal hair, consisting of:
    an effective amount of tea-polyphenol and,or tea-pigment;
    an effective amount of a metal salt; and
    auxiliary components acceptable in a hair dyeing product.

2. A combination product for dyeing human or animal hair, comprising:
    a hair softening preparation; and
    the dyeing product of claim 1 as a dye preparation and a mordant preparation.

3. The combination product according to claim 2, wherein the hair softening preparation includes one or more selected from a disulfide linkage reducing agent, an alkalizer, a penetration enhancer, and a thickener.

4. A process for dyeing human or animal hair comprising use of the dyeing product of claim 1.

5. The process according to claim 4, wherein the tea-polyphenol is selected from one or more of flavanols, anthocyanins, flavonoids, flavonols and phenolic acids, and
    the effective amount of the tea-polyphenol, based on catechin, relative to the total weight of the product, is 0.5% to 15% by weight.

6. The process according to claim 5, wherein the tea-polyphenol is flavanols, and is selected from one or more of epigallocatechin, epicatechin, epigallocatechin gallate, and epicatechin gallate.

7. The process according to claim 4, wherein the tea-pigment is selected from one or more of theaflavins, thearubigins and theabrownins, and
    the effective amount of the tea-pigment, based on theaflavins, relative to the total weight of the product, is 0.5% to 15% by weight.

8. The process according to claim 4, wherein the metal salt is a ferrous salt, and
    the effective amount of the ferrous salt, based on ferrous ion, relative to the total weight of the product, is 1% to 10% by weight.

* * * * *